United States Patent

Asberom et al.

[11] Patent Number: 5,952,349
[45] Date of Patent: Sep. 14, 1999

[54] MUSCARINIC ANTAGONISTS FOR TREATING MEMORY LOSS

[75] Inventors: Theodros Asberom, West Orange; Derek B. Lowe, Kenilworth, both of N.J.; Michael J. Green, Encinitas, Calif.

[73] Assignee: Schering Corporation, Kenilworth, N.J.

[21] Appl. No.: 08/889,486

[22] Filed: Jul. 8, 1997

Related U.S. Application Data

[60] Provisional application No. 60/021,691, Jul. 10, 1996.

[51] Int. Cl.$^6$ ......................... A61K 31/445; C07D 401/04
[52] U.S. Cl. ......................... 514/316; 514/314; 514/320; 514/321; 514/323; 546/152; 546/179; 546/193; 546/196; 546/197; 546/201
[58] Field of Search ................................. 514/314, 316, 514/320, 321, 323; 546/152, 179, 193, 196, 197, 201

[56] References Cited

U.S. PATENT DOCUMENTS 4,942,169  7/1990  Sugimoto et al. ................ 514/318

FOREIGN PATENT DOCUMENTS 711763      5/1996   European Pat. Off. .
4202185     7/1992   Japan .
WO 96/26196 8/1996   WIPO .

OTHER PUBLICATIONS

Sugasawa et al. "1, 4–benzodiazepine derivatives" CA 102:6558, 1984.
Sugasawa et al. "1–azacycloakly–1,4–benzodiazepin–2ones with antianxiety antidepressant action" CA 103:37458, 1985.
Baumgold et al, *Eur. J. Pharmacol.*, 251 (1994), pp. 315–317.
Melchiorre et al, *J. Med. Chem.*, 36 (1993), pp. 3734–3737.
Logermann et al, Brit. J. Pharmacol., 17 (1961), pp. 286–296.
Cheng et al, *Biochem. Pharmacol.*, 22 (1973), pp. 3099–3108.
Watson et al, *J. Pharmacol. Exp. Ther.*, 237 (1986), pp. 411–418.
Wilkerson et al, *J. Med. Chem.*, 36 (20) (1993), pp. 2899–2907.
Vidaluc et al, *J. Med. Chem.*, 37 (5) (1994), pp. 689–695.
Drukarch et al, *Eur. J. Pharmacol.*, 141 (1–2) (1987), pp. 153–157.
Provan et al, *Brit. J. Pharmacol.*, 111(4) (1994), pp. 1103–1110.

*Primary Examiner*—Ceila Chang
*Attorney, Agent, or Firm*—Anita W. Magatti

[57] ABSTRACT

1,4 Di-substituted piperidine muscarinic antagonists of formula I

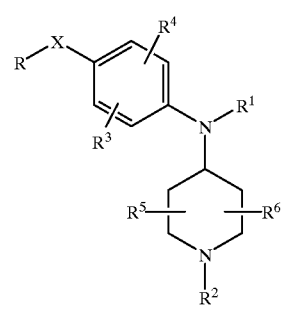

or a pharmaceutically acceptable salt, ester, or solvate thereof, wherein X is a bond, —O—, —$SO_{0-2}$—, —CO—, —C($OR^7$)$_2$—, —$CH_2$—O—, —O—$CH_2$—, —CH=CH—, —$CH_2$—, —CH($C_1$—$C_6$ alkyl)—, —C($C_1$—$C_6$ alkyl)$_2$—, —CO$NR^{17}$—, —$NR^{17}$CO—, —$SO_2NR^{17}$— or —$NR^{17}SO_2$—; R is $C_3$—$C_6$ cycloalkyl, optionally substituted phenyl or optionally substituted pyridyl; $R^1$ is H, —CN, —$CF_3$, alkyl, cycloalkyl, cycloalkenyl, alkenyl, —$COR^{15}$, —COO(alkyl, aryl, heteroaryl, alkylaryl or alkylheteroaryl), alkylaryl, alkylheteroaryl or —CON($R^{13}$)$_2$; $R^2$ is cycloalkyl, cycloalkenyl, t-butoxycarbonyl or optionally substituted 4-piperidinyl; and $R^3$, $R^4$, $R^5$, $R^6$, $R^7$, $R^{13}$, $R^{15}$ and $R^{17}$ are as defined in the specification are disclosed as being useful for treating cognitive disorders such as Alzheimer's disease; also disclosed are pharmaceutical compositions, methods of preparation and combinations of compounds of formula I capable of enhancing ACh release with ACh'ase inhibitors.

14 Claims, No Drawings

MUSCARINIC ANTAGONISTS FOR TREATING MEMORY LOSS

This application is a provisional of 60-021,691 filed Jul. 10, 1996.

BACKGROUND OF THE INVENTION

The present invention relates to 1,4-di-substituted piperidines useful in the treatment of cognitive disorders, pharmaceutical compositions containing the compounds, methods of treatment using the compounds, and to the use of said compounds in combination with acetylcholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity in improving learning and memory against cognitive disorders. Baumgold et al. (Eur. J. of Pharmacol., 251, (1994) 315–317) disclose 3-α-chloroimperialine as a highly selective m2 muscarinic antagonist.

The present invention relates to a class of 1,4-di-substituted piperidines, some of which have m2 selectivity even higher than that of 3-α-chloroimperialine. Logemann et al (Brit. J. Pharmacol. (1961), 17, 286–296) describe certain di-N-substituted piperazines, but these are different from the inventive compounds of the present invention. Furthermore, the compounds of Logemann et al. are not disclosed to have activity against cognitive disorders.

SUMMARY OF THE INVENTION

The present invention relates to compounds according to the structural formula I,

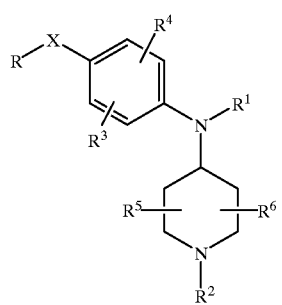

I or an isomer, pharmaceutically acceptable salt, ester or solvate thereof, wherein X is a bond, —O—, —S—, —SO—, —SO$_2$—, —CO—, —C(OR$^7$)$_2$—, —CH$_2$—O—, —O—CH$_2$—, —CH=CH—, —CH$_2$—, —CH(C$_1$—C$_6$ alkyl)—, —C(C$_1$—C$_6$ alkyl)$_2$—, —CONR$^{17}$—, —NR$^{17}$CO—, —SO$_2$NR$^{17}$— or —NR$^{17}$S(O$_2$—;

R is C$_3$—C$_6$ cycloalkyl,

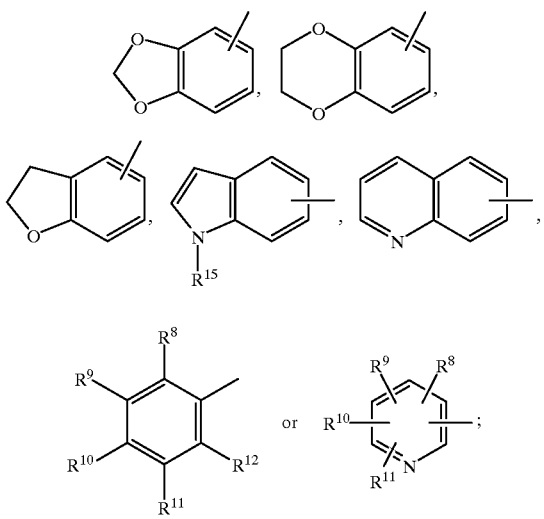

R$^1$ is H, —CN, —CF$_3$, C$_1$—C$_6$ alkyl, C$_3$—C$_6$ cycloalkyl, C$_3$—C$_6$ cycloalkenyl, C$_3$—C$_6$ alkenyl, —COR$^{15}$, —COO(C$_1$—C$_6$ alkyl), —COO(aryl), —COO(heteroaryl), —COO((C$_1$—C6 alkyl)aryl), —COO((C$_1$—C$_6$ alkyl)heteroaryl), —(C$_1$—C$_6$ alkyl)aryl, —(C$_1$—C$_6$ alkyl)heteroaryl or —CON(R$^{13}$)$_2$;

R$^2$ is C$_3$—C$_6$ cycloalkyl, C$_3$—C$_6$ cycloalkenyl, t-butoxycarbonyl or

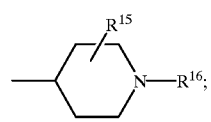

R$^3$ and R$^4$ are independently selected from the group consisting of H, halo, —CF$_3$, C$_1$—C$_6$ alkyl, C$_1$—C$_6$ alkoxy and —OH;

R$^5$ and R$^6$ are independently selected from the group consisting of H, C$_1$—C$_6$ alkyl, —CF$_3$, C$_1$—C$_6$ alkoxy, —OH, C$_1$—C$_6$ alkylcarbonyl, C$_1$—C$_6$ alkoxycarbonyl, R$^{13}$CONH—, R$^{14}$OCONH—, R$^{13}$NHCONH— and NH$_2$CONR$^{13}$—;

R$^7$ is independently selected from the group consisting of H and alkyl, provided that both R$^7$ groups are not H; or the two R$^7$ groups may be joined to form —(CH2)p— wherein p is an integer of 2 to 4;

R$^8$, R$^9$, R$^{10}$, R$^{11}$ and R$^{12}$ are independently selected from the group consisting of H, halo, C$_1$—C$_6$ alkyl, C$_1$—C$_6$ alkoxy, benzyloxy, benzyloxy substituted by —NO$_2$ or —N(R$^{14}$), halo C$_1$—C$_6$ alkyl, polyhalo C$_1$—C$_6$ alkyl, —NO$_2$, —CN, —SO$_2$, —OH, —NH$_2$, —N(R$^{14}$)$_2$, —HCO, polyhalo C$_1$—C$_6$ alkoxy, acyloxy, (C$_1$—C$_4$ alkyl)$_3$Si—, (C$_1$—C$_6$ alkyl)SO$_{0-2}$, arylsulfonyl, heteroaryl-sulfonyl, acyl, (C$_1$—C$_6$ alkoxy)CO—, —OCON(R$^{14}$)$_2$, —NHCOO—(C$_1$—C$_6$)alkyl, —NHCO—(C$_1$—C$_6$ alkyl), phenyl, hydroxy(C$_1$—C$_6$ alkyl) or morpholino;

R$^{13}$ is independently selected from the group consisting of H, C$_1$—C$_6$ alkyl, C$_3$—C6 cycloalkyl, —(Cl—C6 alkyl) COOR$^{15}$, aryl, heteroaryl, —(C$_1$—C$_6$ alkyl)aryl, —(C$_1$—C$_6$ alkyl)heteroaryl and adamantyl;

R$^{14}$ is independently selected from the group consisting of H and C$_1$—C$_6$ alkyl;

R15 is H, $C_1$—$C_{20}$ alkyl, $C_1$—$C_6$ cycloalkyl, aryl or heteroaryl;

$R^{16}$ is H, $C_1$—$C_6$ alkyl, —$COR^{15}$, $C_1$—$C_6$ alkoxycarbonyl, $(R^{14})_2NCO$— or —$SO_1I_2$—$R^{15}$; and $R^{17}$ is H, $C_1$—$C_6$ alkyl, aryl or heteroaryl.

Preferred compounds of formula I are those wherein X is —SO—, —SO2— or —$CH_2$—. Also preferred are compounds of formula I wherein R is $R^8$, $R^9$, $R^{10}$, $R^{11}$, $R^{12}$-substituted phenyl or 3,4-methylenedioxyphenyl, with 4-methoxyphenyl and 3,4-methylenedioxyphenyl being more preferred. $R^3$ and $R^4$ are preferably each hydrogen. $R^1$ is preferably cyano, $C_1$—$C_6$ alkyl, more preferably methyl, or $C_3$—$C_6$ alkenyl, preferably allyl. $R^2$ is preferably cyclohexyl or

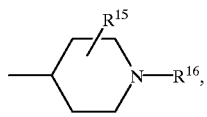

wherein $R^{16}$ is preferably —$COR^{15}$ wherein $R^{15}$ is ethyl or aryl. When $R^{15}$ is aryl, it is preferably $R^8$-substituted aryl, preferably $R^8$-substituted phenyl, especially 2-substituted phenyl wherein the substituent is methyl or halo. The $R^{15}$ substituent attached to a ring carbon of the piperidine ring is preferably hydrogen. $R^5$ and $R^6$ are preferably independently hydrogen and —$CH_3$.

Another aspect of the invention is a pharmaceutical composition comprising a compound having structural formula I in combination with a pharmaceutically acceptable carrier.

Another aspect of the invention is the use of a compound formula I for the preparation of a pharmaceutical composition useful in the treatment of cognitive disorders and neurodegenerative diseases such as Alzheimer's disease.

Another aspect of this invention is a method for treating a cognitive or neurodegenerative disease comprising administering to a patient suffering from said disease an effective amount of a compound of formula I.

Another aspect of this invention is a method for treating cognitive and neurodegenerative diseases, such as Alzheimer's disease with a compound of formula I in combination with an acetylcholinesterase inhibitor.

Another aspect of this invention is a method for treating a cognitive or neurodegenerative disease comprising administering to a patient suffering from said disease an effective amount of a combination of a compound of formula I as defined above, including stereoisomers, pharmaceutically acceptable salts, esters and solvates thereof, said compound being capable of enhancing acetylcholine (ACh) release (preferably an m2 or m4 selective muscarinic antagonist) with an acetycholinesterase (ACh'ase) inhibitor.

Another aspect of this invention is a kit comprising in separate containers in a single package pharmaceutical compounds for use in combination to treat cognitive disorders in one container a compound of formula I capable of enhancing acetylcholine release (preferably an m2 or m4 selective muscarinic antagonist) in a pharmaceutically acceptable carrier and in a second container an acetylcholinesterase inhibitor in a pharmaceutically acceptable carrier, the combined quantities being an effective amount.

DETAILED DESCRIPTION

Except where stated otherwise the following definitions apply throughout the present specification and claims. These definitions apply regardless of whether a term is used by itself or in combination with other terms.

Alkenyl represents a straight or branched hydrocarbon chain of 2 to 6 carbon atoms having at least one carbon-to-carbon double bond.

Cycloalkyl represents a saturated carbocyclic ring having 3 to 6 carbon atoms.

Cycloalkenyl represents a carbocyclic ring having from 3 to 6 carbon atoms and at least he carbon-to-carbon double bond in the ring.

Halo represents fluoro, chloro, bromo or iodo.

Aryl represents optionally substituted phenyl or optionally substituted naphthyl, wherein the substituents are 1 to 3 groups as defined in $R^8$.

Heteroaryl represents optionally substituted heteroaryl groups, wherein the substituents are 1 to 3 groups as defined in $R^8$, and the heteroaryl group is pyridinyl, pyrimidinyl, pyrazinyl, pyridazinyl, thiophenyl, furanyl or pyrolyl.

Polyhalo represent substitution of at least 2 halo atoms to the group modified by the term "polyhalo".

Sulfonyl represents a group of the formula —SO2—.

Sulfonyl represents a group of the formula —SO—.

When a variable appears more than once in the structural formula, for example $R^7$ when X is —$C(OR^7)_2$—, the identity of each variable appearing more than once may be independently selected from the definition for that variable.

Variables $R^5$ and R6 can be attached independently to substitutable carbon atoms in the piperidinyl ring, or both variables can be attached to the same ring carbon atom.

Compounds of this invention may exist in at least two stereo configurations on the carbon to which $R^5$ and/or R6 are attached, except when $R^5$ and $R^6$ are attached to the same carbon and are identical. Further stereoisomerism is present when X is SO, or $C(OR^7)_2$ (when the two $R^7$ groups are not the same). Also within formula I there are numerous other possibilities for stereoisomerism. All possible stereoisomers of formula I are within the scope of the invention.

Compound of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I may be produced by processes known to those skilled in the art as exemplified by the following reaction procedures:

METHOD A

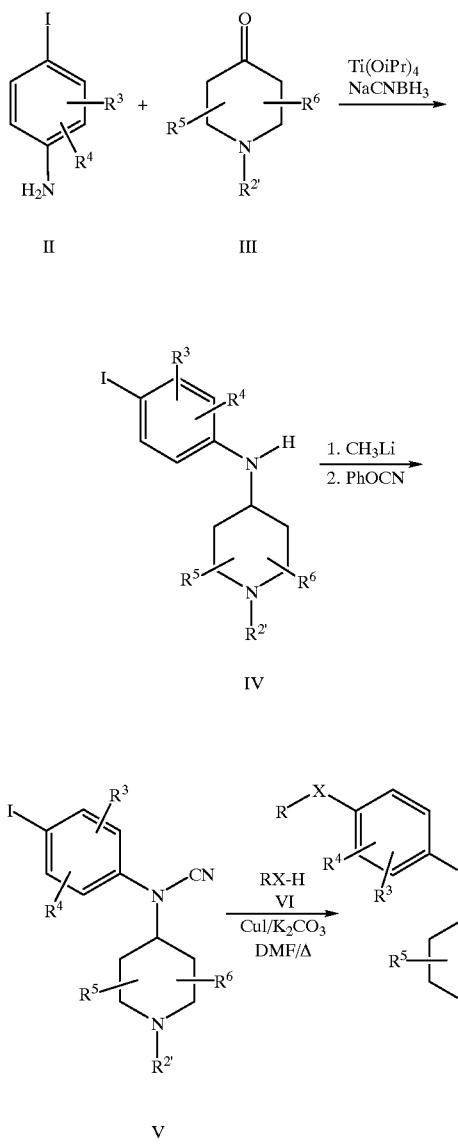

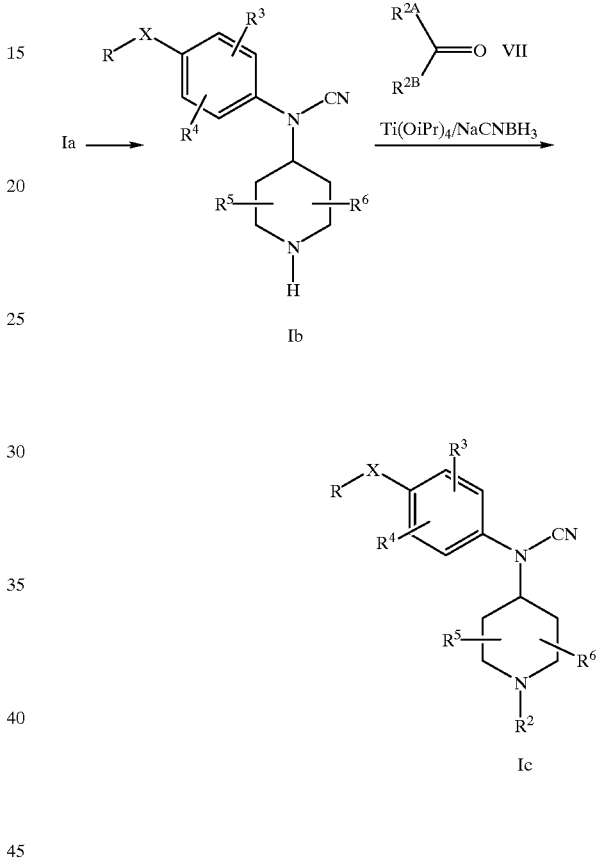

A 4-iodoaniline derivative II is reacted with a piperidone derivative III, wherein $R^{2'}$ is either $R^2$ as previously defined or a suitable nitrogen protecting group, in the presence of a reducing agent such as NaCNBH$_3$, preferably in the presence of a Lewis acid such as titanium isopropoxide to give aniline derivative IV. This is reacted with a strong base such as CH$_3$Li, followed by treatment with phenyl cyanate to give cyanoaniline V. A solution of compound V is then heated with compound VI, wherein R and X are as defined above, in the presence of a catalyst such as copper (I) iodide and a base such as K$_2$CO$_3$ to give compound Ia, wherein $R^1$ is cyano and the remaining variables are as defined above.

When R2' is a nitrogen protecting group, compound Ia can be transformed into compounds of formula Ib by removal of the protecting group, followed by treating Ib with a ketone VII, wherein $R^{2A}$ and $R^{2B}$, together with the carbon to which they are attached, form a group $R^2$ as previously defined, under conditions as described in Scheme A-1 to give a compound of formula Ic, wherein $R^1$ is cyano and the remaining variables are as defined above.

METHOD B

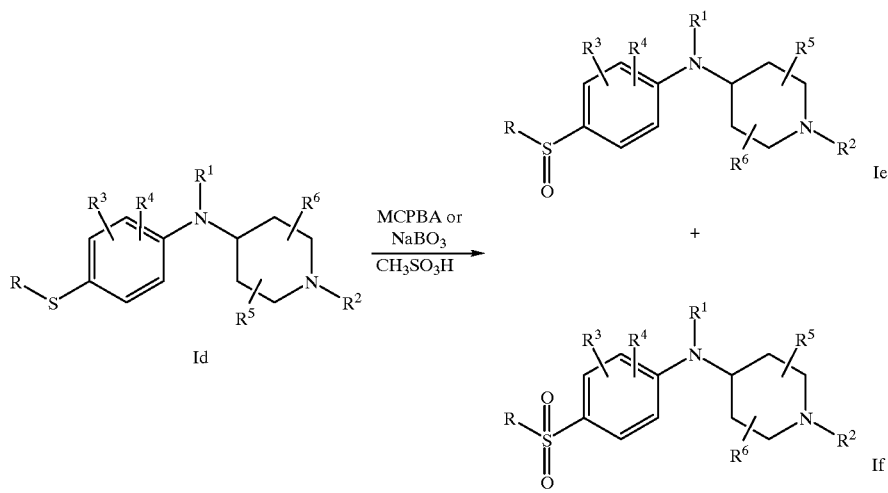

Compounds of type Id, wherein X is —S— and all other variables are as previously defined, can be transformed into compounds of type Ie and If, wherein X is —S(O)— or —S(O)$_2$—, by treating Id with a suitable oxidant such as m-chloroperbenzoic acid or NaBO$_3$, preferably in the presence of an acid such as CH$_3$SO$_3$H or acetic acid.

METHOD C

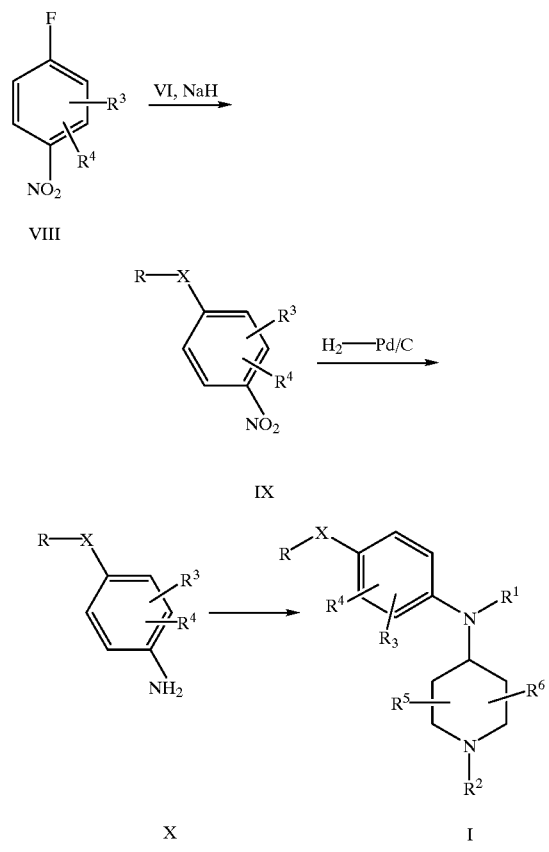

Compounds of formula I can also be made by treatment of a 4-fluoronitrobenzene, VIII, with a compound of formula VI, as previously defined, in the presence of a strong base such as NaH to give a substituted nitrobenzene derivative IX. The nitro group is then reduced to the aniline X under standard conditions, such as treatment with H$_2$ gas in the presence of a catalyst such as palladium on charcoal. Compound X can be converted to various compounds of formula I using the procedures described in Methods A, B, D and F.

METHOD D

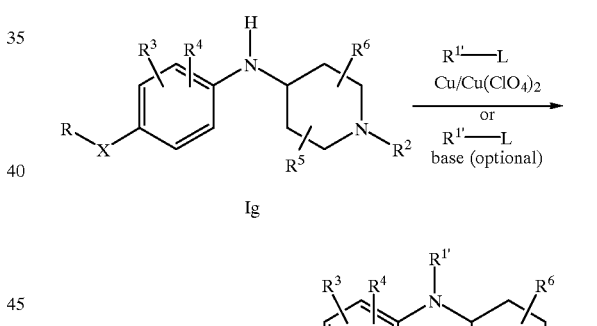

Compounds of formula Ig, wherein R$^1$ is H and all other variables are as previously defined, can be transformed into compounds of type Ih, wherein R$^{1'}$ is alkyl or alkenyl, by:

Method D-1: Treatment of Ig with an alkenylating agent R$^{1'}$-L, wherein L is a halogen, preferably iodine or bromine, in the presence of a mixture of Cu$^0$ and Cu(ClO$_4$)$_2$; or Method D-2: Reaction of an alkylating agent R$^{1'}$-L with Ig, where Ig is either used in excess or optionally in the presence of an added base such as CH$_3$Li.

METHOD E

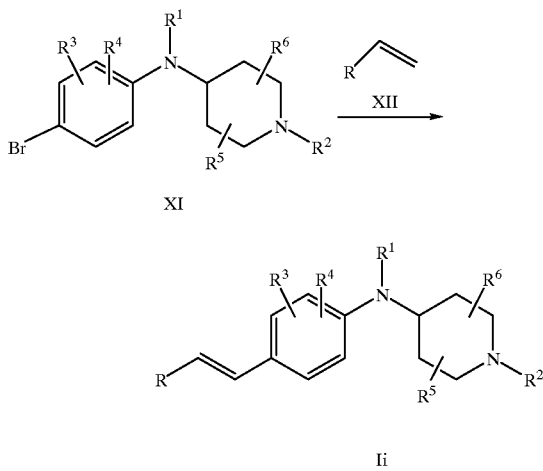

Compounds of type Ii, wherein X is —CH=CH—, can be prepared by treating an aryl bromide XI (prepared according to Method A-1, steps 1 and 2) with an olefin XII in the presence of a catalyst such as palladium acetate.

METHOD F

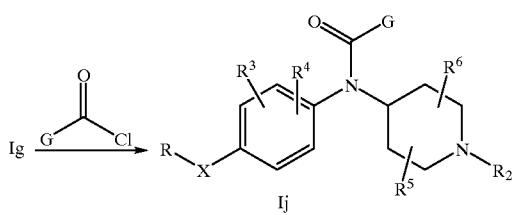

Compounds of formula Ij, wherein G is alkyl, aryl, arylalkyl, alkoxy, aryloxy or arylalkoxy as defined above, can be prepared by treating compound Ig with an acylating agent G(CO)Cl (i.e., an acid chloride or a chloroformate) in a suitable solvent such as $CH_2Cl_2$.

METHOD G

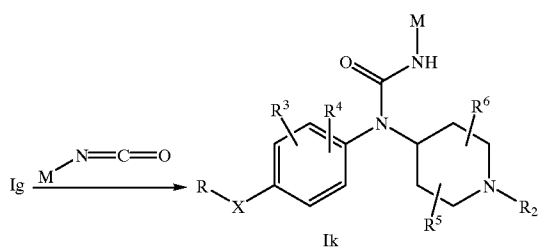

Compounds of type Ik, wherein M is alkyl, aryl, or arylalkyl, can be prepared by heating compound Ig with an isocyanate M—N=C=O in a suitable solvent such as $CH_3CN$ or toluene at a temperature sufficient to effect reaction, such as 80°–150° C.

METHOD H

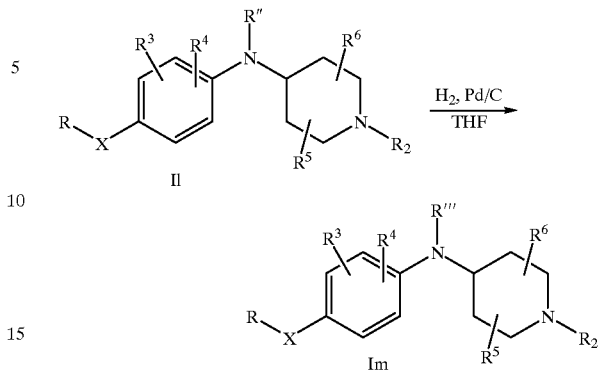

Compounds of formula Im, wherein R''' is alkyl or cycloalkyl, can be prepared by hydrogenation of the corresponding compound of formula Il, wherein R'' is alkenyl or cycloalkenyl, in the presence of a suitable catalyst such as palladium on carbon in a suitable solvent such as THF or ethanol.

METHOD I

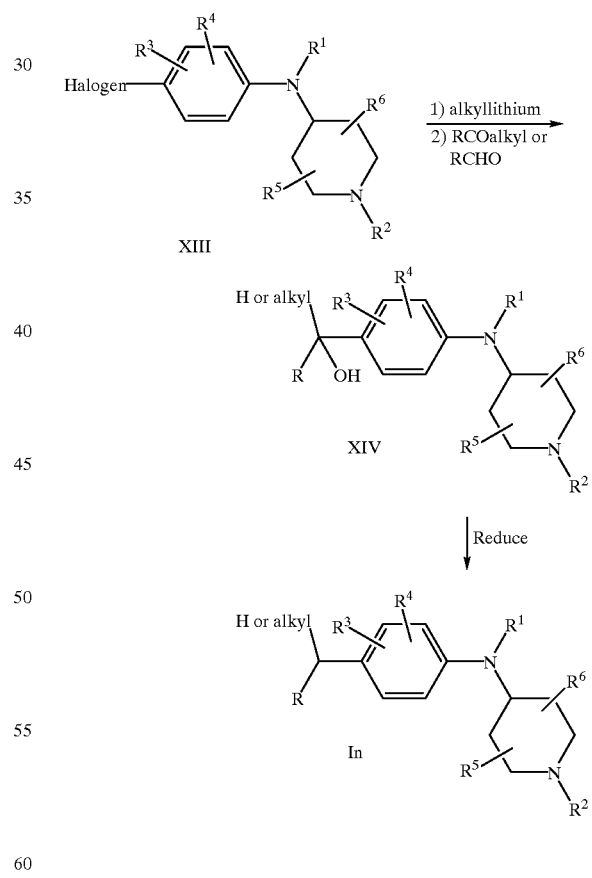

Compounds of type In can be prepared by treating a compound of formula XIII (prepared from compound II of reaction scheme A-1 using various methods, particularly Methods A, D, F, and/or G) with an alkyllithium reagent such as n-butyllithium or t-butyllithium in a suitable solvent such as diethyl ether or THF a low temperature, such as −78° C. to 0° C. The resulting anion is treated with an aldehyde RCHO or a ketone RCO-alkyl, wherein R is as defined above, to give a carbinol of formula XIV. The carbinol is treated with a suitable reducing agent, preferably triethylsilane in the presence of a strong acid such as trifluoroacetic acid to give In.

As indicated, in the above processes it is sometimes desirable and/or necessary to protect certain groups during the reactions. Conventional protecting groups, familiar to those skilled in the art, are operable.

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

The compounds of formula I exhibit selective m2 and/or m4 muscarinic antagonizing activity, which has been correlated with pharmaceutical activity for treating cognitive disorders such as Alzheimers disease and senile dementia.

The compounds of formula I display pharmacological activity in test procedures designated to indicate m1, m2 and m4 muscarinic antagonist activity. The compounds are non-toxic at pharmaceutically therapeutic doses.

For preparing pharmaceutical compositions from the compounds of formula I capable of enhancing ACh release, and ACh'ase inhibitors, pharmaceutically acceptable inert carriers are admixed with the active compounds. The pharmaceutically acceptable carriers may be either solid or liquid. Solid form preparations include powders, tablets, dispersible granules, capsules, cachets and suppositories. A solid carrier can be he or more substances which may also act as diluents, flavoring agents, solubilizers, lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

When a compound of formula I capable of enhancing ACh release is used in combination with an ACh'ase inhibitor to treat cognitive disorders, these two active components may be co-administered simultaneously or sequentially, or a single pharmaceutical composition comprising a compound of formula I capable of enhancing ACh release and an ACh'ase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the ACh'ase inhibitor may range from 0.001 to 100 mg/kg body weight.

The invention disclosed herein is exemplified by the following preparations and examples which should not be construed to limit the scope of the disclosure. Alternative mechanistic pathways and analogous structures may be apparent to those skilled in the art.

EXAMPLE 1

Ethyl 4-[cyano[4-[(4-methoxyphenyl)thio]phenyl] amino ]-[1,4'-bipiperidine]-1'-carboxylate Step 1:

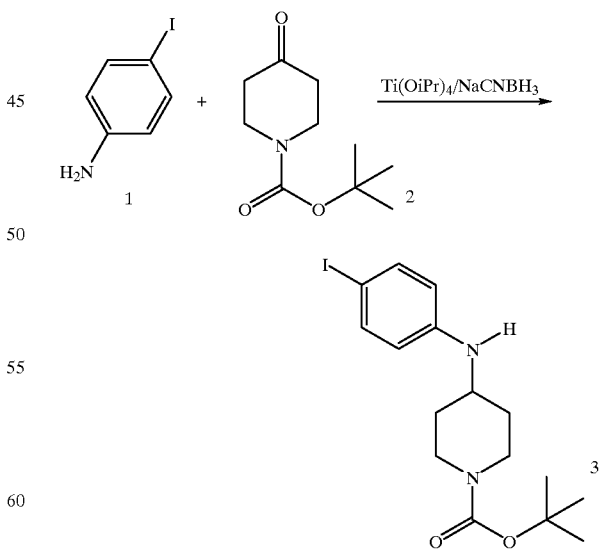

To a solution containing 4-iodoaniline 1 (8.8 g, 40.2 mmol) and N-tert-butoxycarbonyl-4-piperidone 2 (8.0 g, 40.2 mmol) in anhydrous $CH_2Cl_2$ (80 ml), add $Ti(O—iPr)_4$ (13.7 g, 48.2 mmol). Stir the resulting purple solution at room temperature under $N_2$ for 12 h. After cooling to 0° C., treat the mixture with a solution of $NaCNBH_3$ (8.3 g, 132.6 mmol) in $CH_3OH$ (30 ml) and stir at room temperature overnight. Quench with 600 ml mixture of water/EtOAc (1:3), and then remove the insoluble substances by filtration through a bed of Celite®. Separate the organic phase, wash with brine, dry with $Na_2SO_4$ and remove the solvent to obtain 16.7 g of the crude product, which is chromatographed on silica gel using EtOAc/hexane (1:4) as the eluent to give 8.3 g (49%) of the product 3 as white solid.

Step 2:

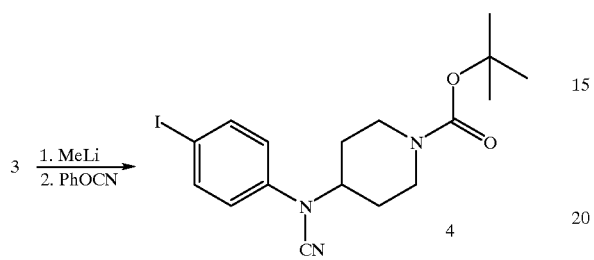

To a dry flask kept under a static pressure of $N_2$ add anhydrous THF (250 ml) and 3 (15.0 g, 37.0 mmol), cool to −78° C., and add 1M $CH_3Li$ in hexane (26 ml, 37.0 mmol) at a rate such that the reaction temperature is maintained below −65 C. Add phenyl cyanate (6.7 g, 56.0 mmol) at such a rate as to prevent the reaction from exotherming above −60° C. and stir for 1 h. Allow the resulting solution to come to room temperature and stir overnight. Pour the reaction mixture into water and extract with EtOAc. Wash the combined extracts once with brine, dry over anhydrous $Na_2SO_4$, remove the solvent and flash chromatograph the residue on silica gel eluting with EtOAc:hexanes (1:4) to give 8.25 g (52%) of the product 4 as off-white solid.

Step 3:

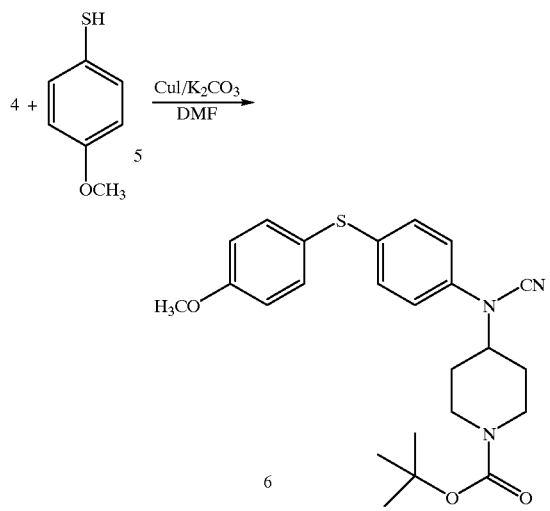

Stir a mixture of 4 (5.0 g, 12.0 mmol), 4-methoxythiophenol 5 (1.96 g 14.0 mmol), CuI (2.67 g, 14.0 mmol), anhydrous $K_2CO_3$ (6.60 g, 48.0 mmol) and DMF (6 ml) at 110° C. for 6 h under $N_2$, monitoring the progress of the reaction by TLC. Cool, add water (50 ml) and benzene (50 ml) with stirring and remove the insoluble substances by filtration. Separate the organic phase, wash with brine, and dry with $Na_2SO_4$. Remove the solvent under reduced pressure to give a brown oil residue and purify by chromatography on silica gel, eluting with hexane/EtOAc (5:1) to give the sulfide 6 (2.6 g, 49 %) as colorless oil.

Step 4:

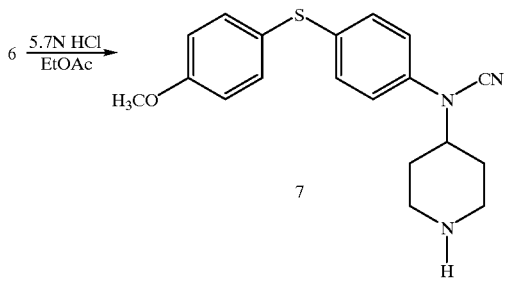

Stir a solution of 6 (2.6 g, 5.91 mmol) in EtOAc (50 ml) containing 5.7N HCl (20.5 ml) at room temperature for 4 h. Cool the reaction mixture and basify to pH 8 with a saturated solution of $NaHCO_3$. Separate the organic phase, wash with brine and dry with $Na_2SO_4$ to give 1.7 g (85 %) of the product 7 as yellow oil.

Step 5:

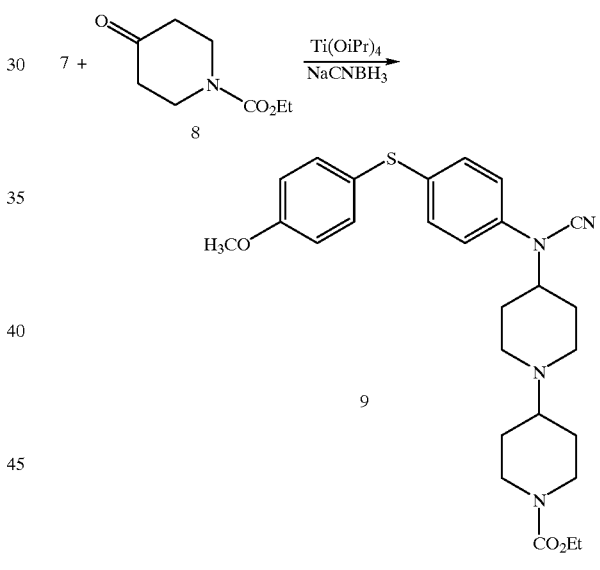

To a mixture containing 7 (1.1 g, 3.24 mmol), N-carbethoxy-4-piperidone 8 (1.66 g, 9.72 mmol) and Ti(O—iPr)$_4$ (4.61 g, 16.20 mmol), add enough dry $CH_2Cl_2$ (15 ml) to enable smooth stirring. Stir at room temperature under $N_2$ for 12 h, cool the mixture (0° C.) and treat with a solution of $NaBH_3CN$ (1.0 g,16.20 mmol) in $CH_3OH$ (6 ml). Stir at room temperature for 12 h, and quench the reaction with 300 ml of EtOAc/water (3:1). Remove the insoluble substances by filtration through a bed of Celite®. Separate the organic phase, wash with brine and dry with $Na_2SO_4$. Remove the solvent to obtain a yellow oil and purify by chromatography on silica gel using EtOAc/hexane (9:1) as the eluent to give 820 mg (51 %) of 9 as sticky white solid.

Using a similar procedure, compounds of the following structure are prepared

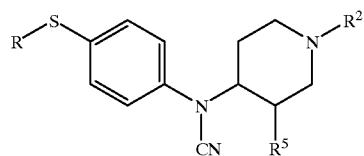
wherein the variables are as defined in the table:
| Ex. | R | R² | R⁵ | HRMS calc'd | HRMS found |
|---|---|---|---|---|---|
| 1A | H₃CO–C₆H₄– | cyclohexyl | H | 422.2266 | 422.2258 |
| 1B | H₃CO–C₆H₄– Isomer A | —CH₂C₆H₅ | —CH₃ | 444.2110 | 444.2099 |
| 1C | H₃CO–C₆H₄– Isomer B | —CH₂C₆H₅ | H | 444.2110 | 444.2108 |
| 1D | C₆H₅– | cyclohexyl | H | 392.2160 | 392.2160 |
| 1E | 3,5-Cl₂–C₆H₃– | cyclohexyl | H | 460.1381 | 460.1374 |
| 1F | (CH₃)₃C–C₆H₄– | cyclohexyl | H | 448.2786 | 448.2780 |
| 1G | 3,4-methylenedioxyphenyl | cyclohexyl | H | 436.2059 | 436.2052 |
| 1H | Cl–C₆H₄– | cyclohexyl | H | 426.1771 | 426.1771 |
| 1I | cyclohexyl | cyclohexyl | H | 398.2630 | 298.2636 |
| 1J | H₃C–C(O)–NH–C₆H₄– | cyclohexyl | H | 449.2375 | 449.2367 |

-continued

| Ex. | R | R² | R⁵ | HRMS calc'd | HRMS found |
|---|---|---|---|---|---|
| 1K | F₃CO—⟨phenyl⟩— | | H | 476.1983 | 473.1987 |

(R² = cyclohexyl)

Again using a similar procedure, compounds of the following structure are prepared

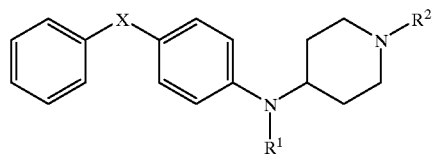

wherein the variables are as defined in the table:

| Ex. | X | R¹ | R² | Data |
|---|---|---|---|---|
| 1L | —O— | —CN | —C(O)OC(CH₃)₃ | mp = 109–111° C. |
| 1M | —O— | —CN | cyclohexyl | mp = 248–252° C. (dec.) |
| 1N | —CH₂O— | —CN | cyclohexyl | HRMS calc'd: 476.2008 found: 476.2010 |
| 1O | —CH₂O— | —CH₃ | cyclohexyl | HRMS calc'd: 379.2749 found: 379.2748 |

EXAMPLE 2

Ethyl 4-[cyano[4-[(4-methoxyphenyl)sulfinyl]phenyl]amino][1,4'-bipiperidine]-1'-carboxylate and Ethyl 4-[cyano[4-[(4-methoxyphenyl)sulfonyl]phenyl]amino][1,4'-10 bipiperidine]-1'-carboxylate

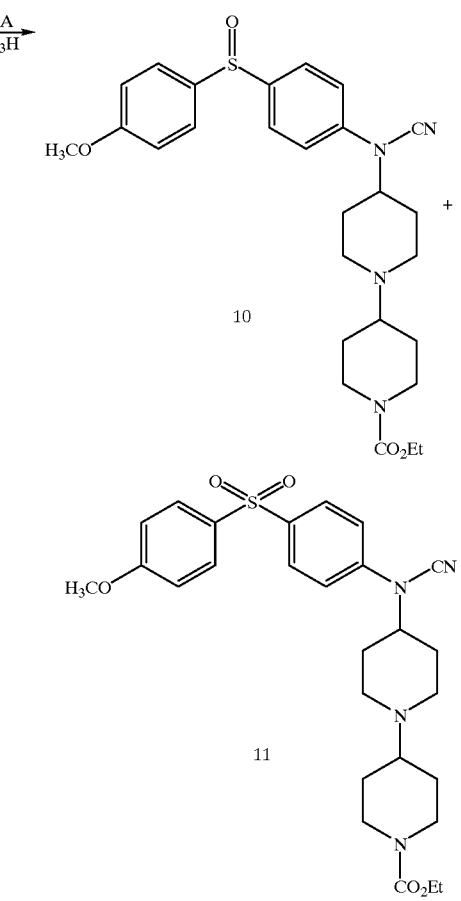

To an ice-cold solution of thioether 9 from Example 1 (750 mg, 1.52 mmol) in anhydrous $CH_2Cl_2$ (15 ml) containing $CH_3SO_3H$ (9.1 ml, 4.56 mmol), add 70–75 % m-chloroperbenzoic acid (520 mg, 2.27 mmol). Stir at 0° C. for 30 min, then at room temperature for 50 min, then cool the reaction mixture to 0° C. and basify to pH 8 with saturated $NaHCO_3$. Separate the organic phase, wash with brine and dry with $Na_2SO_4$. Remove the solvent to give 730 mg of white solid. Purify by chromatography on silica gel using 2.5 % $CH_3OH$ in $CH_2Cl_2$ as the eluent to give 255 mg of the sulfone 11, followed by 305 mg of the sulfoxide 10.

10: HRMS for $C_{27}H_{35}N_4O_4S$ calc'd: 511.2379; found 511.2381

11: HRMS for $C_{27}H_{35}N_4O_5S$ calc'd: 527.2328; found 527.2324

Using a similar procedure, compounds of the following structure are prepared

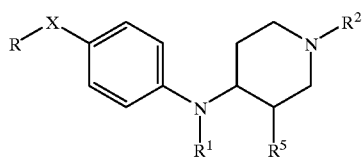

wherein the variables are as defined in the following table:

| Ex. | R | X | $R^1$ | $R^2$ | $R^5$ | Data |
|---|---|---|---|---|---|---|
| 2C | H₃CO-C₆H₄- | —SO₂— | —CN | cyclohexyl | H | HRMS calc'd: 454.2164 found: 454.2150 |
| 2D | H₃CO-C₆H₄- | —SO— | —CN | cyclohexyl | H | HRMS calc'd: 438.2215 found: 438.2230 |
| 2E | H₃CO-C₆H₄- | —SO— | —CN | cyclohexyl | H | — |
| 2F | H₃CO-C₆H₄- | —SO— | —CN | cyclohexyl | H | — |
| 2G | H₃CO-C₆H₄- | —SO₂— | —CH₃ | cyclohexyl | H | HRMS calc'd: 443.2368 found: 443.2376 |
| 2H | H₃CO-C₆H₄- | —SO— | —CH₃ | cyclohexyl | H | HRMS calc'd: 427.2419 found: 427.2422 |
| 2I | H₃CO-C₆H₄- | —SO₂— | —CH₂—CH=CH₂ | cyclohexyl | H | HRMS calc'd: 469.2525 found: 469.2533 |
| 2J | H₃CO-C₆H₄- | —SO— | —CH₂—CH=CH₂ | cyclohexyl | H | HRMS calc'd: 453.2576 found: 453.2566 |
| 2K | H₃CO-C₆H₄- | —SO— | —CN | —CH₂C₆H₅ | H | HRMS calc'd: 446.1902 found: 446.1904 |

-continued

| Ex. | R | X | R¹ | R² | R⁵ | Data |
|---|---|---|---|---|---|---|
| 2L | H₃CO—C₆H₄— | —SO— | —CN | —CH₂C₆H₅ | —CH₃ | HRMS calc'd: 460.2059 found: 460.2054 |
| 2M | H₃CO—C₆H₄— | —SO₂— | —CN | —CH₂C₆H₅ | —CH₃ | HRMS calc'd: 476.2008 found: 476.2010 |
| 2N | H₃CO—C₆H₄— | —SO— | —CN | —CH₂C₆H₅ | —CH₃ | HRMS calc'd: 460.2059 found: 460.2050 |
| 2O | C₆H₅— | —SO— | —CN | cyclohexyl | H | HRMS calc'd: 408.2110 found: 408.2112 |
| 2P | H₃CO—C₆H₄— | —SO₂— | —C(O)CH₂ | cyclohexyl | H | MS (Cl)m + 1 = 471, 429, 306, 299, 225, 179, 134, 109 |
| 2Q | H₃CO—C₆H₄— | —SO— | —C(O)CH₂ | cyclohexyl | H | MS (Cl)m + 1 = 455, 439, 397, 301, 274, 225, 166, 134, 109 |
| 2R | F₃C—C₆H₄— | —SO— | —CN | cyclohexyl | H | HRMS calc'd: 476.1983 found: 476.1982 |
| 2S | C₆H₅— | —SO₂— | —CN | cyclohexyl | H | HRMS calc'd: 424.2059 found: 424.2060 |
| 2T | H₃CO—C₆H₄— | —SO₂— | —CH₂C₆H₅ | cyclohexyl | H | MS (FAB)m + 1 = 519.2, 503.2, 429.1, 367.2, 289.1, 257.1, 232.1 |
| 2U | H₃CO—C₆H₄— | —SO— | —CH₂C₆H₅ | cyclohexyl | H | MS (FAB)m + 1 = 502.3, 488, 443, 396.2, 340.1, 320.1 |

-continued

| Ex. | R | X | R₁ | R² | R⁵ | Data |
|---|---|---|---|---|---|---|
| 2V | H₃CO—C₆H₄— | —SO— | —C(O)OCH₂CH₃ | cyclohexyl | H | MS (FAB)m + 1 = 485.2, 469.2, 395.2, 378.2, 331.2, 320.1, 273.1, 257.1, 232.1 |
| 2W | H₃CO—C₆H₄— | —SO₂— | —C(O)OCH₂CH₃ | cyclohexyl | H | MS (FAB)m + 1 = 501.2, 485.2, 419.2, 394.2, 347.2, 320.1, 274.1, 257.1, 232.1 |
| 2X | F₃C—C₆H₄— | —SO₂— | —CN | cyclohexyl | H | HRMS calc'd: 492.1933 found: 492.1932 |
| 2Y | H₃CO—C₆H₄— | —SO₂— | —CO(CH₂)₈CH₃ | cyclohexyl | H | MS (FAB)m + 1 = 583.3, 567.4, 447.4, 431.3, 413.4, 293.1, 246.1, 237.1 |
| 2Z | H₃CO—C₆H₄— | —SO— | —CO(CH₂)₈CH₃ | cyclohexyl | H | MS (FAB)m + 1 = 567.4, 485.3, 402.3, 391.3, 347.2, 232.2, 216.3, 164.2, 137.2 |
| 2AA | 3,5-Cl₂-C₆H₃— | —SO₂— | —CN | cyclohexyl | H | HRMS calc'd: 492.1279 found: 492.1282 |
| 2AB | (CH₃)₃C—C₆H₄— | —SO₂— | —CN | cyclohexyl | H | MS MH + 480 (100%) |
| 2AC | 3,4-methylenedioxyphenyl | —SO₂— | —CN | cyclohexyl | H | — |

-continued

| Ex. | R | X | R¹ | R² | R⁵ | Data |
|---|---|---|---|---|---|---|
| 2AD | 4-H₃CO-C₆H₄- | —SO₂— | -C(=O)-cyclohexyl | cyclohexyl | H | MS (FAB)m + 1 = 539.8, 523.9, 432.4, 385.2, 248.9, 234.9 |
| 2AE | 4-H₃CO-C₆H₄- | —SO— | -C(=O)-cyclohexyl | cyclohexyl | H | — |
| 2AF | 4-H₃CO-C₆H₄- | —SO₂— | -C(=O)-NH-phenyl | cyclohexyl | H | — |
| 2AG | 4-Cl-C₆H₄- | —SO— | —CN | cyclohexyl | H | HRMS calc'd: 442.1720 found: 442.1732 |
| 2AH | 4-Cl-C₆H₄- | —SO₂— | —CN | cyclohexyl | H | HRMS calc'd: 458.1669 found: 458.1667 |
| 2AI | 4-H₃CO-C₆H₄- | —SO₂— | -C(=O)-NH-CH₂-phenyl | cyclohexyl | H | — |
| 2AJ | cyclohexyl | —SO— | —CN | cyclohexyl | H | HRMS calc'd: 414.2579 found: 414.2583 |
| 2AK | cyclohexyl | —SO₂— | —CN | cyclohexyl | H | HRMS calc'd: 430.2528 found: 430.2527 |
| 2AL | 4-H₃CO-C₆H₄- | —SO₂— | -C(=O)-NH-CH₃ | cyclohexyl | H | — |
| 2AM | 4-(CH₃C(=O)NH)-C₆H₄- | —SO— | —CN | cyclohexyl | H | MS MH + 466 (100%) |

-continued

| Ex. | R | X | R¹ | R² | R⁵ | Data |
|---|---|---|---|---|---|---|
| 2AN | H₃CO—⟨C₆H₄⟩— | —SO₂— | 4-methoxyphenyl-NHC(O)- | cyclohexyl | H | — |
| 2AO | H₃CO—⟨C₆H₄⟩— | —SO₂— | 3-nitro-ethylphenyl | cyclohexyl | H | MS (FAB)m + 1 = 564.2, 548.3, 463.1, 427.2, 391.3, 324.1, 310.1, 293.1 |
| 2AP | F₃CO—⟨C₆H₄⟩— | —SO— | —CN | cyclohexyl | H | HRMS calc'd: 492.1933 found: 492.1932 |
| 2AQ | F₃CO—⟨C₆H₄⟩— | —SO₂— | —CN | cyclohexyl | H | HRMS calc'd: 508.1882 found: 508.1884 |
| 2AR | H₃CO—⟨C₆H₄⟩— | —SO₂— | —CN | cyclohexyl | —CH₃ | HRMS calc'd: 468.2321 found: 468.2329 |

EXAMPLE 3

Step 1:

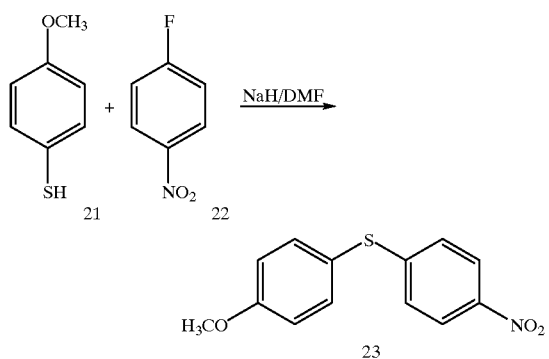

To an ice-cold suspension of NaH (7.1 g, 0.178 mol) in anhydrous DMF (125 ml), add 4-methoxy-benzenethiol 21 (25.0 g, 0.178 mol) dropwise over 45 min, and stir the mixture at room temperature for 30 min. Cool the reaction mixture in an ice-bath, and treat with neat 1-fluoro-4-nitrobenzene 22 (25.2 g, 0.178 mol). Stir the resulting mixture at room temperature overnight, pour into water (1100 ml) and extract with EtOAc (3×500 ml). Dry the combined organic layers with Na₂SO₄ and remove the solvent to give 43 g (92%) of the product 23 as yellow crystals.

Step 2:

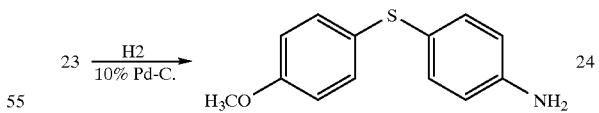

To a suspension of 23 (13.2 g, 50.0 mmol) in EtOH (125 ml), add 10% Pd on carbon (1.3 g) and hydrogenate the mixture at 60 psi for 12 h. Remove the catalyst by filtration through a bed of Celite® and evaporate the solvent to give 11.5 g (100%) of the product 24 as dark yellow solid.

Step 3:

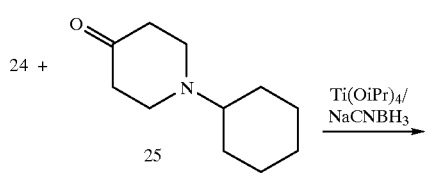

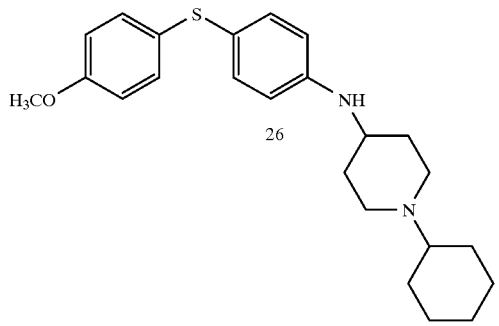

React aniline 24 with N-cyclohexyl-4-piperidinone derivative 25 as described in Example 1, step 1, to give substituted aniline derivative 26.

-continued

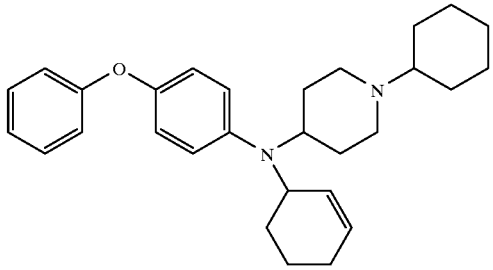

Add a mixture of amine 12 (3.0 g, 8.2 mmol), prepared from 4-phenoxyaniline and N-carboethoxy-4-piperidinone using the procedures of Example, step 1, and cyclohexenyl bromide (875 mg, 5.4 mmol) in EtOAc (30 ml) to a well stirred suspension of copper (II) perchlorate hexahydrate (1.0 g, 2.7 mmol) and copper metal (207 mg, 3.3 mmol) in EtOAc (15 ml) under $N_2$. After stirring at room temperature for 12 hours, add an aqueous solution of KCN (5.5 g in 70 ml of water). Extract the resultant clear solution with EtOAc (2×100 ml). Dry the combined organic extracts with $Na_2SO_4$ and remove the solvent by distillation. Chromatograph the residue on silica gel using EtOAc/hexane (110) as the eluent to give 1.25 g (52%) of the product 13 as semi-solid foam.

Use a similar procedure to prepare compound 4A:

4A  mp = 89–92° C.

EXAMPLE 4

1,1-Dimethylethyl 4-[2-cyclohexen-1-yl-(4-phenoxyphenyl)amino]-1-piperidinecarboxylate

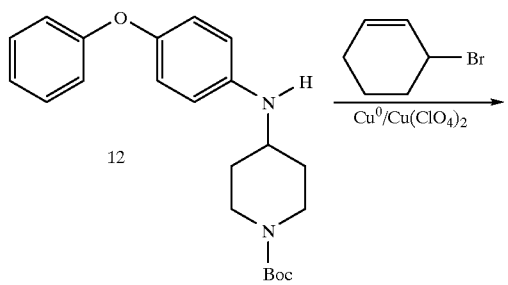

EXAMPLE 5

1-Cyclohexyl-N-[4-[(4-methoxyphenyl)thio]phenyl]-N-[(3-nitrophenyl)methyl]-4-piperidineamine

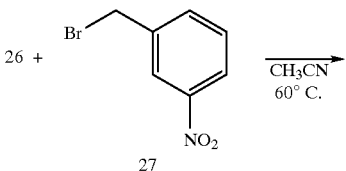

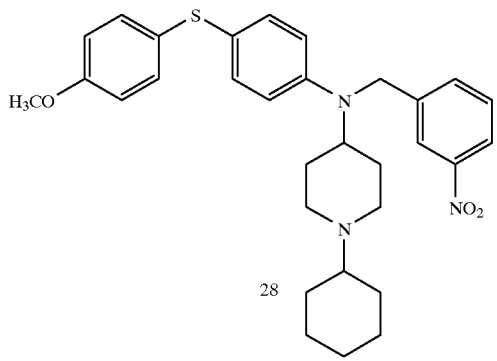

28

Dissolve aniline 26 (500 mg, 1.3 mmol) from Example 3 and 3-nitrobenzylbromide 27 (270 mg) in CH$_3$CN (10 ml). Heat the solution at 60° C. for 3 h. After cooling to room temperature, add water (50 ml) and basify the solution with saturated aqueous K$_2$CO$_3$. Extract with CH$_2$Cl$_2$ (3×, 30 mls), combine the organic extracts, dry with Na$_2$SO$_4$ and evaporate to obtain an orange oil (830 mg). Purify the crude material by chromatography using CH$_2$Cl$_2$:EtOH:NH$_4$OH (100:3:1) as eluant to obtain compound 28 as a yellow oil, 370 mg (55%). MS (FAB)m+1=532.2, 516.2, 449.2, 369.2, 307.1, 293.1, 263.0, 215.1.

Use a similar procedure to prepare compounds 5A, 5B and 5C:

5A
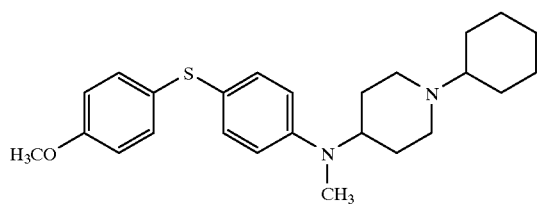
HRMS for C$_{25}$H$_{35}$N$_2$OS: calc'd: 411.2470; found 411.2460

5B
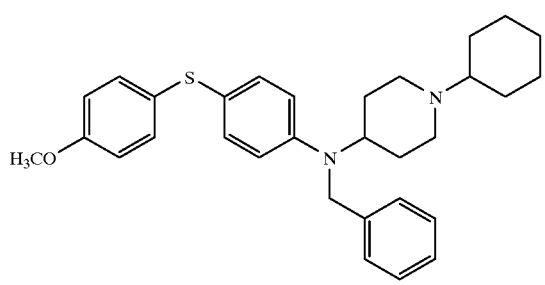
MS (Cl)m + 1 = 439.1, 425.1, 395.1, 357.1, 332.1, 299.0, 273.0, 246.1, 212.1

5C
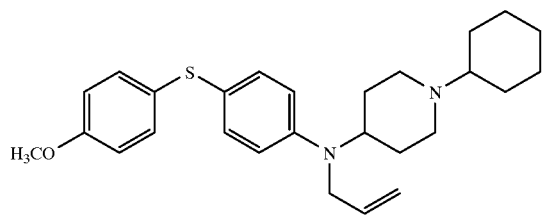
HRMS for C$_{27}$H$_{37}$N$_2$OS: calc'd: 437.2627; found 437.2624

EXAMPLE 6

(1-Cyclohexyl-4-piperidinyl)[4-[(E)-2-(4-methoxyphenyl)-ethenyl]phenyl]cyanamide

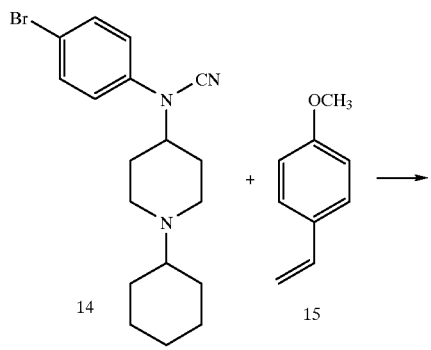

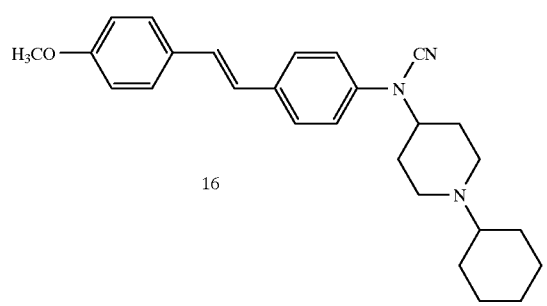

Heat a mixture of p-bromoaniline 14 (100 mg, 0.28 mmol), 4-vinylanisole 15 (479 mg, 0.37 mmol), palladium diacetate (0.64 mg, 0.003 mmol), tri-o-tolylphosphine (1.7 mg, 0.004 mmol), and dry $Et_3N$ (0.3 ml) at 110° C. for 72 h in a capped heavy-wall tube flushed with dry $N_2$. To the cooled mixture, add water and $CH_2Cl_2$. Extract the water layer with $CH_2Cl_2$ (2×10 ml), wash the combined $CH_2Cl_2$ solutions with water, dry over $MgSO_4$ and evaporate. Chromatograph the residue on silica gel using EtOAc/hexane (1:10) as the eluent to give the product 16 (61.1 mg, 53%) as white powder.

HRMS for $C_{27}H_{34}N_3O$: calc'd 416.2702; found 416.2688.

EXAMPLE 7

N-(1-cyclohexyl-4-piperidinyl)-N-[4-[(4-methoxyphenyl)thio]-phenyl]decanamide

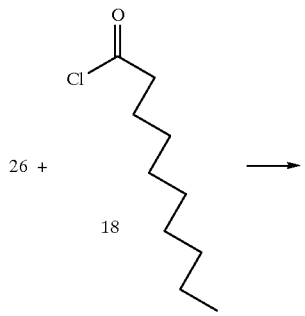

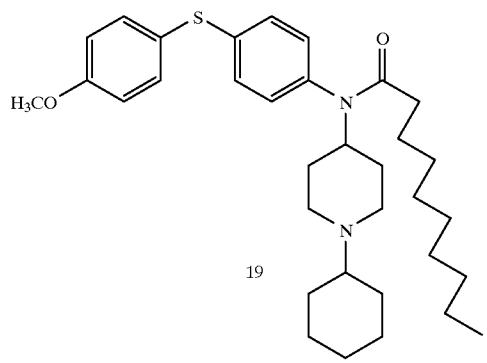

Reflux a solution of aniline 26 from Example 3 (0.67 g, 1.7 mmoles) and acid chloride 18 (0.32 g, 1.7 mmoles) in $CH_2Cl_2$ (10 ml) for 4 to 5 hours. After cooling, add water (10 ml), then basify with solid $K_2CO_3$. Extract the aqueous layer with $CH_2Cl_2$ (2×10 ml). Dry the organic layer and evaporate the solvent to obtain the crude amide. Purify by chromatography using $CH_2Cl_2$:EtOH:$NH_4OH$ (100:3:1) as eluent. MS (FAB)m+1=551.3, 395.2, 284.1, 209.2, 166.1, 122.1.

Using a similar procedure, compounds of the following structure are prepared

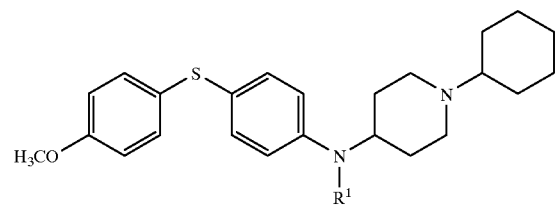

wherein $R^1$ is as defined in the table:

| Ex. | $R^1$ | Data |
|---|---|---|
| 7A | —C(O)CH$_3$ | MS (FAB) m + 1 = 439.1, 425.1, 395.1, 357.1, 332.1, 299.0, 273.0, 246.1, 212.1 |
| 7B | —C(O)CH$_2$CH$_3$ | MS (FAB) m + 1 = 469.2, 386.3, 303.1, 232.1 |
| 7C | —C(O)-cyclohexyl | MS (FAB) m + 1 = 507.3, 395.2, 387.3, 304.1, 273.1, 257.1, 232.1 |
| 7D | —C(O)CH(CH$_3$)$_2$ | MS(FAB) m + 1 = 467.4, 385.3, 360.3, 307.2, 257.2, 246.2, 232.1 |

EXAMPLE 8

N-(1-Cyclohexyl-4-piperidinyl)-N'-(4-methoxyphenyl)-N-[4-[(4-methoxyphenyl)thio]phenyl]urea

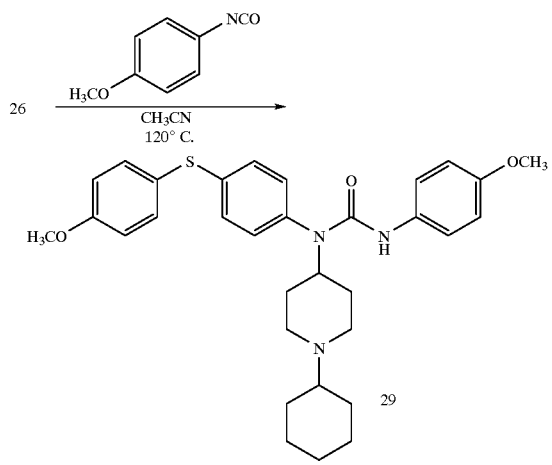

Place a solution of aniline 26 (0.33 mmoles) from Example 3 and 4-methoxy-phenylisocyanate (0.5 mmoles) in CH$_3$CN (1.5ml) in a sealed vial and heat in an oil bath at 120° C. for 3 h. Allow the mixture to cool to room temperature and let stand overnight. Filter the resultant precipitate and wash with cold CH$_3$CN to give the chromatographically pure urea 29 (TLC, eluting with CH$_2$Cl$_2$:EtOH:NH$_4$OH (100:3:1)).

Using a similar procedure, compounds of following structure are prepared,

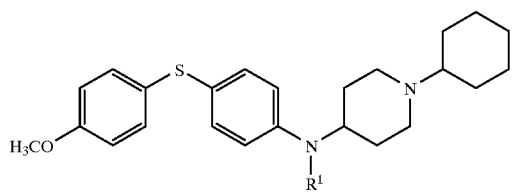

wherein the variable R$^1$ is as defined in the table:

| Ex. | R$^1$ | Data |
|---|---|---|
| 8A | —C(O)NHCH$_3$ | MS (FAB) m + 1 = 454.3, 396.2, 347.2, 289.1, 246.1, 232.1 |
| 8B | | — |
| 8C | —C(O)NHCH$_2$C(O)OCH$_2$CH$_3$ | — |

-continued

| Ex. | R$^1$ | Data |
|---|---|---|
| 8D | | — |
| 8E | | — |
| 8F | | — |

EXAMPLE 9

N,N'-Dicyclohexyl-N-(4-phenoxyphenyl)-4-piperidinamine

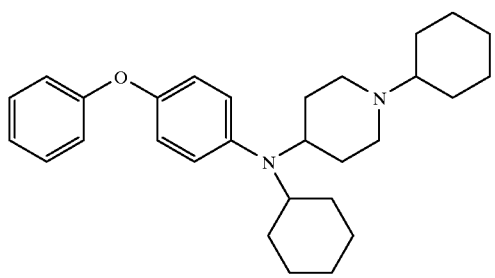

Hydrogenate a mixture of the product of Example 4A (56.9 mg, 0.13 mmol) and 10% Pd/C (8 mg) in THF (2 mL) at 1 atm pressure of H$_2$ for 5 h. Filter the mixture through Celite®, wash the Celite® with CH$_2$Cl$_2$ and concentrate the filtrate to obtain 54.1 mg of the product as a colorless oil. HRMS for C$_{29}$H$_{41}$N$_2$O: calc'd: 433.3219; found 433.3212.

EXAMPLES 10A to D

Using a procedure similar to that described in Example 1, compounds of the following formula are prepared:

wherein the variables are as defined in the table:

| Ex. | R[16] | HRMS calc'd | HRMS found |
|---|---|---|---|
| 10A | (2-methylbenzoyl) | 587.2328 | 587.2316 |
| 10B | (2-chlorobenzoyl) | 607.1782 | 607.1769 |
| 10C | $CH_3CH_2SO_2$ | 561.1842 | 561.1848 |
| 10D | $CH_3(CH_2)_2SO_2$ | 575.1998 | 575.2006 |

EXAMPLE 11

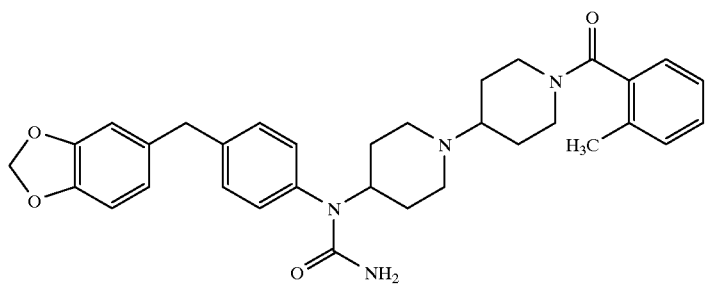

Step 1:

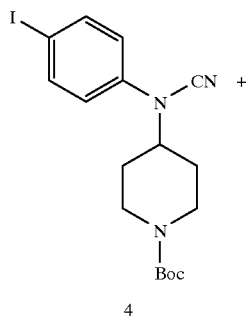

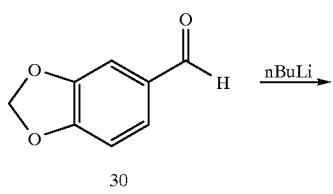

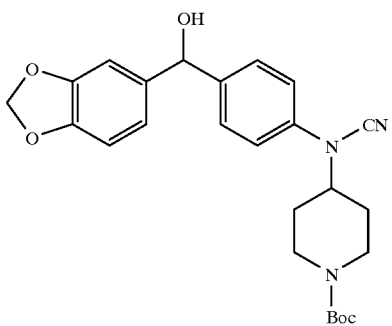

To a solution of 4 (1.0 g, 2.34 mmol) in anhydrous THF (10.0 ml) at −78° C. was added n—BuLi (0.94 ml, 2.34 mmol, 2.5M hexane). The resulting bright yellow mixture was stirred for 10 min., then was treated with a solution of piperinal 30 (281 mg, 1.87 mmol) in THF (3.0 ml). The mixture was stirred at −78° C. for 1 hr, then warmed to room temperature overnight. The mixture was quenched with sat. $NH_4Cl$, the THF was evaporated and the aqueous residue was extracted with EtOAc (3X). The combined organic phase was washed with water and brine, dried over $Na_2SO_4$, filtered and the solvent was removed to obtain 1.07 g of crude product, which was chromatographed on silica gel using EtOAc/hexane (1:4) as the eluent to give 240 mg (28%) of the product 31 as a yellow solid.

Step 2:

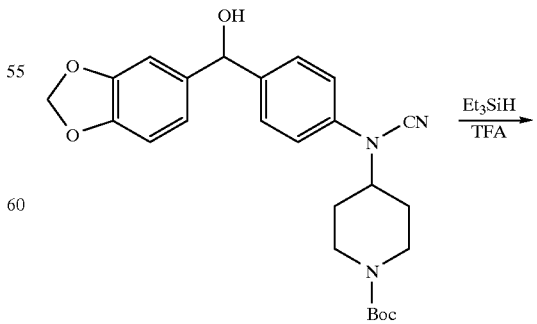

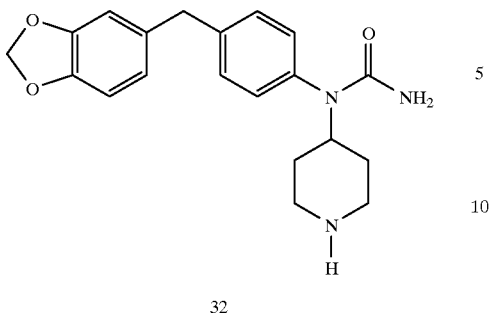

32

To a solution of 31 (240 mg, 0.53 mmol) in CH$_2$Cl$_2$ (10.0 ml) was added Et$_3$SiH (1.1 g, 9.53 mmol) followed by trifluoroacetic acid (6.04 g, 53.0 mmol). The resulting yellow solution was heated at reflux 12 hrs, then cooled to room temperature. Most of the volatiles were evaporated and the residue basified to pH 8 with 1.0N NaOH. The residue was extracted with EtOAc (4X) while saturating the aqueous phase with NaCl crystals. The combined organic phase was dried over Na$_2$SO$_4$, filtered and concentrated to give 220 mg of product 32 as a yellow oil.

Step 3:

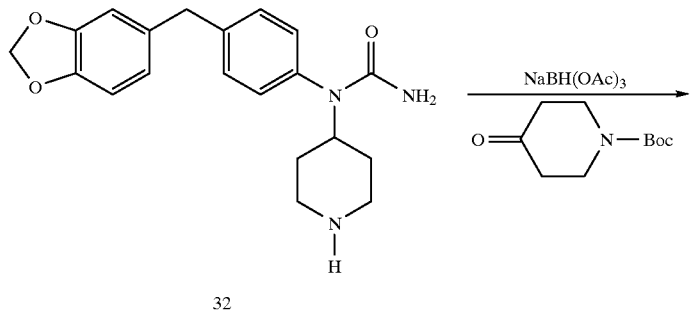

32

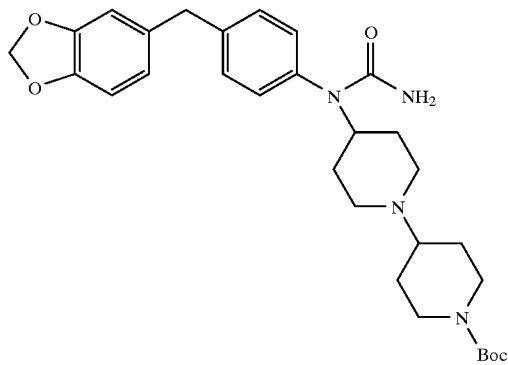

33

To a solution of amine 32 (240 mg, 0.72 mmol) in CH$_2$Cl$_2$ (4.0 ml) was added a solution of N—Boc—4-piperidone (215 mg, 1.08 mmol) in CH$_2$Cl$_2$ (2.0 ml) followed by glacial acetic acid (0.16 ml, 2.88 mmol). The mixture was stirred at room temperature for 30 min, then NaBH(OAc)$_3$ (456 mg, 2.16 mmol) was added and stirring at room temperature was continued for 12 hr. The reaction mixture was diluted with EtOAc and washed with 1N NaOH (3X). The organic phase was dried over Na$_2$SO$_4$, filtered and concentrated to 620 mg of yellow solid. The crude product was flash chromatographed on silica gel, eluting with EtOH:EtOAc (20:80) to afford 115 mg (31%) of product 33 as a white solid.

Step 4:

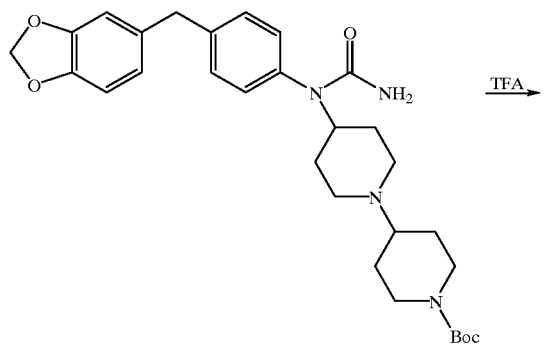

33

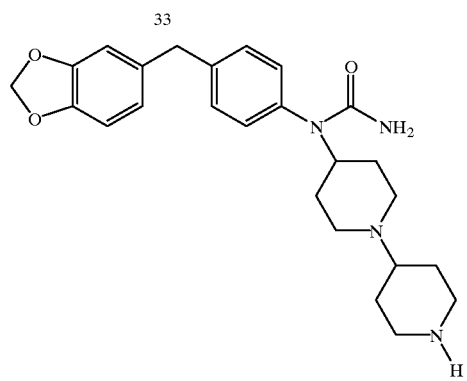

34

To a solution of amine 33 (110 mg, 0.21 mmol) in anhydrous CH$_2$Cl$_2$ (2.0 ml) was added CF$_3$CO$_2$H (0.16 mmol, 2.1 mmol). The resulting mixture was stirred at room temperature for 1 hr, then quenched with water. The biphasic mixture was basified with 1N NaOH, extracted with CH$_2$Cl$_2$ (3X), the combined organic phase was dried over Na$_2$SO$_4$ and evaporated to give 59 mg (67%) of product 34 as a yellow solid.

Step 5:

To a solution of amine 34 (43 mg, 0.10 mmol) in CH$_2$Cl$_2$ (1.5 ml) containing Et$_3$N (12.1 mg, 0.12 mmol) was added o-toluoyl chloride (18.6 mg, 0.12 mmol). The yellow mixture was stirred at room temperature for 1 hr. The crude reaction mixture was directly applied on a prep TLC plate (2000 micron) and eluted with EtOH:EtOAc (20:80) to give 25 mg (45%) of the title compound as yellow viscous oil.

Similarly, prepare the compounds of the following formula:

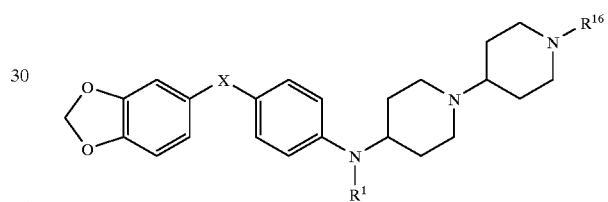

wherein X, R$^1$ and R$^{16}$ are as defined in the following table:

| Ex. | X | R$^1$ | R$^{16}$ | HRMS calc'd | HRMS found |
|---|---|---|---|---|---|
| 11A | —CH$_2$— |  | H | 437.2553 | 437.2555 |
| 11B | —CH$_2$— |  |  | 537.3077 | 537.3090 |

| Ex. | X | R₁ | R¹⁶ | HRMS calc'd | HRMS found |
|---|---|---|---|---|---|
| 11C | —CH₂— | —CH₃ | 2-methylbenzoyl group | 526.3070 | 526.3072 |
| 11D | —CH₂— | —CH₃ | benzo[b]thiophene-2-carbonyl group | 568.2634 | 568.2634 |

Following are descriptions of the pharmacological test procedures.

MUSCARINIC BINDING ACTIVITY

The compound of interest is tested for its ability to inhibit binding to the cloned human m1, m2 and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homgenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using 3H-quinuclidinyl benzilate (QNB) (Watson et al., 1986). Briefly, membranes (approximately 8, 20, and 14 μg of protein assay for the m1, m2, and m4 containing membranes, respectively) were incubated with ³H—QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for IC$_{50}$ values (i.e. the concentration of compound required to inhibit binding by 50%) using the EBDA computer program (McPherson, 1985). Affinity values (K$_i$) were then determined using the following formula (Cheng and Prusoff, 1973);

$$K_i = \frac{IC_{50}}{1 + \left[\frac{\text{concentration of radioligand}}{\text{affinity } (K_D) \text{ of radioligand}}\right]}$$

Hence a lower value of K$_i$ indicates greater binding affinity.

The following publications, the entire contents of which are incorporated herein by reference, explain the procedure in more detail.

Cheng, Y.-C. and Prusoff, W. H., Relationship between the inhibitory constant (K$_i$) and the concentration of inhibitor which causes 50 per cent inhibition (IC$_{50}$) of an enzymatic reaction. Biochem. Pharmacol. 22: 3099–3108, 1973.

McPhersh, G. A. Kinetic, EBDA, Ligand, Lowry: A Collection of Radioligand Binding Analysis Programs. Elsevier Science Publishers BV, Amsterdam, 1985.

Watson, M. J, Roeske, W. R. and Yamamura, H. I. [³H] Pirenzepine and (-)[³H]quinuclidinyl benzilate binding to rat cerebral cortical and cardiac muscarinic cholinergic sites. Characterization and regulation of antagonist binding to putative muscarinic subtypes. J. Pharmacol. Exp. Ther. 237: 411–418,1986.

To determine the degree of selectivity of a compound for binding the m2 receptor, the K$_i$ value for m1 receptors was divided by the K$_i$ value for m2 receptors. A higher ratio indicates a greater selectivity for binding the m2 muscarinic receptor. A similar calculation is made to determine the m4 selectivity.

MICRODIALYSIS METHODOLOGY

The following procedure is used to show that a compound functions as an m2 antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12,3 mm×0.5 mm) to a depth of 3 mm in striatum beyond the end of the guide. The probe was connected beforehand with tubing to a microinjection pump (CMA-/100). Rats were collared, tethered, and, following probe insertion, were placed in a large, clear, plexiglass bowl with litter material and access to food and water. The probe was perfused at 2 μl/min with Ringer's buffer (NaCl 147 mM; KCl 3.0 mM; CaCl$_2$ 1.2 mM; MgCl$_2$ 1.0 mM) containing 5.5 mM glucose, 0.2 mM L-ascorbate, and 1 μM neostigmine bromide at pH 7.4). To achieve stable baseline readings, microdialysis was allowed to proceed for 90 minutes prior to the collection of fractions. Fractions (20 μl) were obtained at 10 minute intervals over a 3 hour period using a refrigerated collector (CMA/1 70 or 200). Four to five baseline fractions were collected, following which the drug or combination of drugs to be tested was administered to the animal. Upon completion of the collection, each rat was autopsied to determine accuracy of probe placement.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic m2 receptor antagonism.

For preferred compounds of formula I, the following values for $K_i$ binding to m1, m2 and m4 receptors were found, and the selectivity ratios calculated:

| Ex. | $K_i$, nM, m1 | $K_i$, nM, m2 | m2 Selectivity Ratio ($K_i$,m1/$K_i$,m2) | $K_i$, nM, m4 | m4 Selectivity Ratio ($K_i$,m4/$K_i$,m2) |
|---|---|---|---|---|---|
| 1N | 667.2 | 40.8 | 16.4 | 66.4 | 1.6 |
| 2E | 189.0 | 9.0 | 21.0 | 39.3 | 4.4 |
| 2G | 285 | 15.2 | 18.8 | 50 | 3.3 |
| 2I | 47.1 | 3.7 | 12.7 | 10.1 | 2.7 |
| 2AC | 10.0 | 0.44 | 22.7 | 1.60 | 3.6 |
| 2AK | 232.5 | 18.8 | 17.2 | 25.5 | 1.4 |
| 2AM | 212.4 | 13.7 | 15.5 | 41.4 | 3.0 |

Other compounds in accordance with formula I were tested with the following ranges of results:

$K_i$ binding to m1 receptor, nM: 2.3 to 2227 with undetermined values up to >10000.

$K_i$ binding to m2 receptor, nM: 0.44 to 583 with undetermined values up to >4300.

$K_i$ binding to m4 receptor, nM: 0.96 to 1332.5 with undetermined values up to >3000.

Selectivity Ratios m2 Selectivity Ratio:

$K_i$ for m1/$K_i$ for m2: 0.3 to 22.7 without regard to any undetermined $K_i$ values.

m4 Selectivity Ratio:

$K_i$ for m4/$K_i$ for m2: 0.3 to 6.9 without regard to any undetermined $K_i$ values.

Compounds of formula I in combination with an ACh'ase inhibitor have an effect on ACh release. The present invention therefore also relates to administering a compound of formula I in combination with any other ACh'ase inhibitor including, but not limited to, E-2020 (available from Eisai Pharmaceutical) and heptylphysostigmine.

What is claimed:

1. A compound having the structural formula

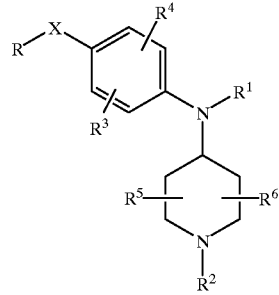

or a pharmaceutically acceptable salt, ester, or solvate thereof, wherein

X is a bond, —O—, —S—, —SO—, —$SO_2$—, —CO—, —C(O$R^7$)$_2$—, —$CH_2$—O—, —O—$CH_2$—, —CH=CH—, —$CH_2$—, —CH($C_1$—$C_6$ alkyl)—, —C($C_1$—$C_6$ alkyl)$_2$—, —CON$R^{17}$—, R is $C_3$—$C_6$ cycloalkyl,

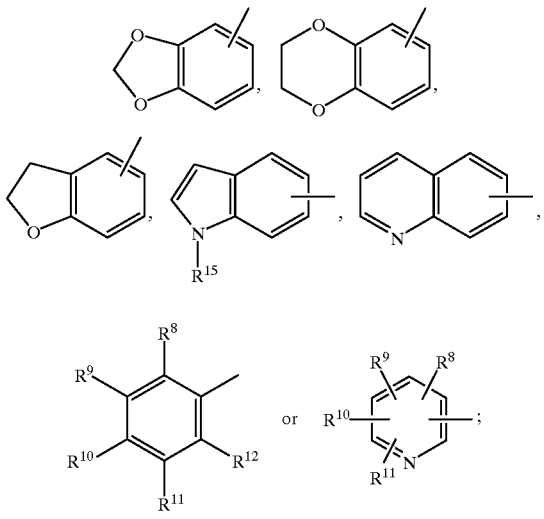

$R^1$ H, —CN, —$CF_3$, $C_1$—$C_6$ alkyl, $C_3$—$C_6$ cycloalkyl, $C_3$—$C_6$ cycloalkenyl, $C_3$—$C_6$ alkenyl, —CO$R^{15}$, —COO($C_1$—$C_6$ alkyl), —COO(aryl), —COO (heteroaryl), —COO(($C_1$—$C_6$ alkyl)aryl), —COO (($C_1$—$C_6$ alkyl)heteroaryl), —($C_1$—$C_6$ alkyl)aryl, —($C_1$—$C_6$ alkyl)heteroaryl or —CON($R^{13}$)$_2$; $R^2$ is $C_3$—$C_6$ cycloalkyl, $C_3$—$C_6$ cycloalkenyl, t-butoxycarbonyl or $R^{15}$.

$R^3$ and $R^4$ are independently selected from the group consisting of H, halo, —$CF_3$, $C_1$—$C_6$ alkyl, $C_1$—$C_6$ alkoxy and —OH;

$R^5$ and $R^6$ are independently selected from the group consisting of H, $C_1$—$C_6$ alkyl, —$CF_3$, $C_1$—$C_6$ alkoxy, —OH, $C_1$—$C_6$ alkylcarbonyl, $C_1$—$C_6$ alkoxycarbonyl, $R^{13}$CONH—, $R^{14}$OCONH—, $R^{13}$NHCONH— and $NH_2CONR^{13}$—;

$R^7$ is independently selected from the group consisting of H and alkyl, provided that both $r^7$ groups are not H; or the two $R^7$ groups may be joined to form —$(CH_2)_p$— wherein p is an integer of 2 to 4:

$R^8 R^9$, $R^{10}$, $R^{11}$ and $R^{12}$ are independently selected from the group consisting of H, halo, $C_1$—$C_6$ alkyl, $C_1$—$C_6$ alkoxy, benzyloxy, benzyloxy substituted by —$NO_2$ or —$N(R^{14})$, halo $C_1$—$C_6$ alkyl, polyhalo $C_1$—$C_6$ alkyl, —$NO_2$, —CN, —$SO_2$,—OH, —$NH_2$,—$N(R^{14})_2$,— HCO, polyhalo $C_1$—$C_6$ alkoxy, acyloxy, $(C_1$—$C_4$ alkyl$)_3$Si—, $(C_1$—$C_6$ alkyl)$SO_{0-2}$, arylsulfonyl, heteroarylsulfonyl, acyl, $(C_1$—$C_6$ alkoxy)CO—, —$OCON(R^{14})_2$, —NHCOO—$(C_1$—$C_6)$alkyl, —NHCO—$(C_1$—$C_6$ alkyl), phenyl, hydroxy$(C_1$—$C_6$ alkyl) or morpholino;

$R^{13}$ is independently selected from the group consisting of H, $C_1$—$C_6$ alkyl, $C_3$—$C_6$ cycloalkyl, —$(C_1$—$C_6$ alkyl)COOR$^{15}$, aryl, heteroaryl, —$(C_1$—$C_6$ alkyl)aryl, —$(C_1$—$C_6$ alkyl)heteroaryl and adamantyl;

$R^{14}$ is independently selected from the group consisting of H and $C_1$—$C_6$ alkyl;

$R^{15}$ is H, $C_1$—$C_{20}$ alkyl, $C_1$—$C_6$ cycloalkyl, aryl or heteroaryl;

$R^{16}$ is H, $C_1$—$C_6$ alkyl, —$COR^{15}$, $C_1$—$C_6$ alkoxycarbonyl, $(R^{14})_2$NCO— or —$SO_{1-2}$—$R^{15}$; and $R^{17}$ is H, $C_1$—$C_6$ alkyl, aryl or heteroaryl;

wherein aryl is phenyl substituted by 1–3 $R^8$ groups or naphthyl substituted by 1–3 $R^8$ groups and heteroaryl is selected from the group consisting of pyridinyl, pyrimidinyl, pyrazinyl, pyridazinyl, thiophenyl, furanyl and pyrrolyl, wherein each heteroaryl group is substituted by 1–3 $R^8$ groups.

2. A compound of claim 1 wherein X is —SO— or —$SO_2$—.

3. A compound of claim 1 wherein R is

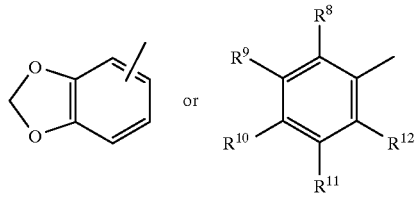

4. A compound of claim 1 wherein $R^3$ and $R^4$ are each hydrogen.

5. A compound of claim 1 wherein $R^1$ is cyano, $C_1$—C6 alkyl or $C_3$—$C_6$ alkenyl.

6. A compound of claim 1 wherein $R^2$ is cyclohexyl or

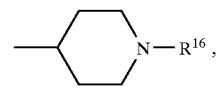

wherein $R^{16}$ is —C(O)—$R^{15}$.

7. A compound of claim 1 wherein $R^5$ and $R^6$ are independently hydrogen or methyl.

8. A compound of claim 1 wherein X is —SO— or —$SO_2$—; R is

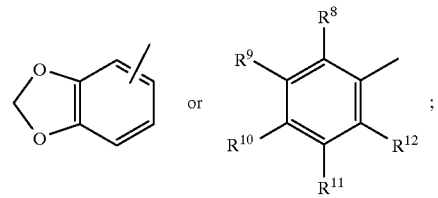

$R^3$ and $R^4$ are hydrogen; $R^1$ is cyano, $C_1$—$C_6$ alkyl or

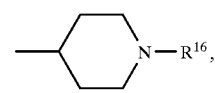

wherein $R^{16}$ is —C(O)—$R^{15}$; and $R^5$ and $R^6$ are independently hydrogen or methyl.

9. A compound of claim 8 wherein R is 3,4-methylenedioxyphenyl or 4-methoxyphenyl and $R^{15}$ is ethyl.

10. A compound as defined in claim 1 selected from the group consisting of compounds represented by the formula

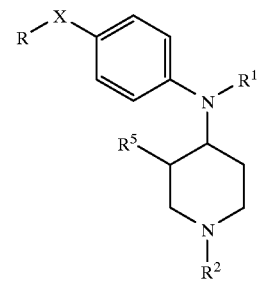

wherein R, X, $R^1$, $R^2$ and $R^5$ are as defined in the following table

| R | X | $R^1$ | $R^2$ | $R^5$ |
|---|---|---|---|---|
| ![methylenedioxyphenyl] | —S— | —CN | ![cyclohexyl] | H |
| | | | — | |

-continued
| R | X | R¹ | R² | R⁵ |
|---|---|---|---|---|
| 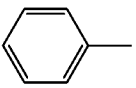 | —O— | —CN | 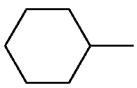 | H |
| 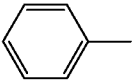 | —CH₂O— | —CN | 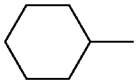 | H |
| 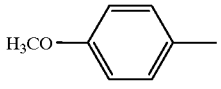 | —SO— | —CN | 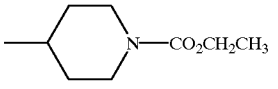 | H |
| 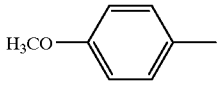 | —SO₂— | —CN | 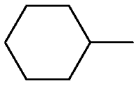 | H |
| 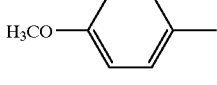 | —SO— | —CN | 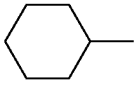 | H |
| 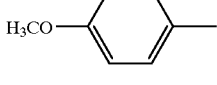 | —SO₂— | —CH₃ | 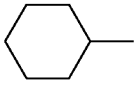 | H |
| 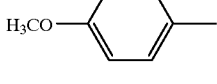 | —SO— | —CH₃ | 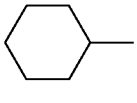 | H |
| 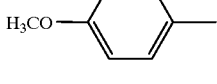 | —SO₂— | —CH₂—CH=CH₂ | 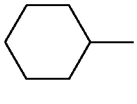 | H |
| 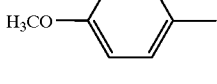 | —SO— | —CH₂—CH=CH₂ | 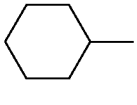 | H |
| 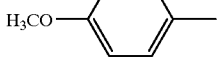 | —SO₂— | —CH₂C₆H₅ | 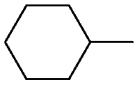 | H |
| 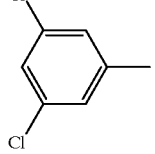 | —SO₂— | —CN | 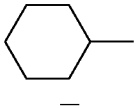 | H |

-continued
| R | X | R¹ | R² | R⁵ |
|---|---|---|---|---|
| 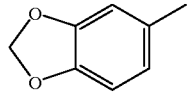 | —SO₂— | —CN | 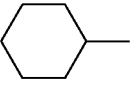 | H |
| 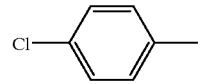 | —SO— | —CN | 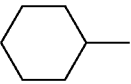 | H |
| 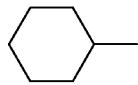 | —SO₂— | —CN | 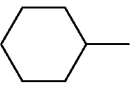 | H |
| 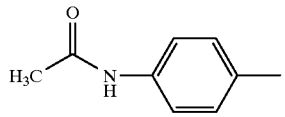 | —SO— | —CN | 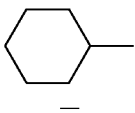 | H |
| 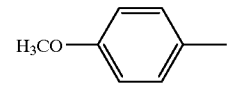 | —SO₂— | —CN | 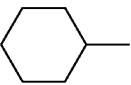 | H |
| 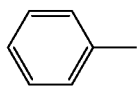 | —O— | 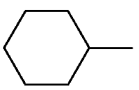 | 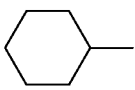 | —CH₃ |
| 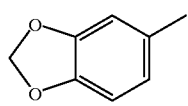 | —CH₂— | —CN | 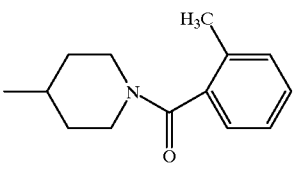 | H |
| 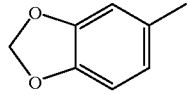 | —CH₂— | —CN | 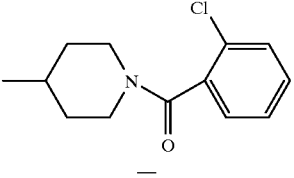 | H |
| 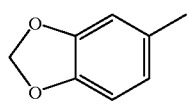 | —SO₂— | —CN | 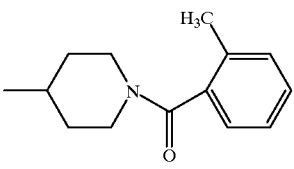 | H |
| 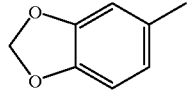 | —SO₂— | —CN | 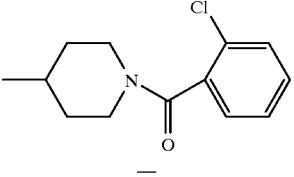 | H |

-continued

| R | X | R¹ | R² | R⁵ |
|---|---|----|----|----|
| 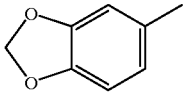 | —CH₂— | —CH₃— | 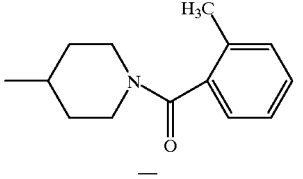 | H |

11. A pharmaceutical composition comprising an effective amount of a compound as defined in claim 1 in combination with a pharmaceutically acceptable carrier.

12. A method for improving learning and memory on Alzheimer's disease comprising administering to a patient suffering from said disease an effective amount of a compound of claim 1.

13. The method of claim 12 wherein the acetylcholine release enhancing compound is an m2 selective muscarinic antagonist.

14. The method of claim 12 wherein the acetylcholine release enhancing compound is an m4 selective muscarinic antagonist.

* * * * *

UNITED STATES PATENT AND TRADEMARK OFFICE
CERTIFICATE OF CORRECTION

PATENT NO : 5,952,349
DATED : SEPTEMBER 14, 1999
INVENTOR(S) : THEODROS ASBEROM, DEREK B. LOWE, MICHAEL J. GREEN

It is certified that error appears in the above-identified patent and that said Letters Patent is hereby corrected as shown below:

In column 46, line 55, delete "$R^2$ is".

In column 46, line 56, before "$C_3-C_6$" insert -- $R^2$ is --. (1st occur.)

In column 46, line 57, delete "or $R^{15}$".

In column 48, line 25, after "or" insert --$C_3-C_6$ alkenyl; $R^2$ is cyclohexyl or--.

Signed and Sealed this

Second Day of May, 2000

Q. TODD DICKINSON

Attest:

Attesting Officer

Director of Patents and Trademarks